United States Patent [19]
Watanabe

[11] Patent Number: 5,837,723
[45] Date of Patent: Nov. 17, 1998

[54] PHARMACEUTICAL COMPOSITION USEFUL FOR TREATING OPHTHALMOLOGICAL DISEASES

[75] Inventor: Toshiaki Watanabe, Yokohama, Japan

[73] Assignee: Mitsubishi Chemical Corporation, Tokyo, Japan

[21] Appl. No.: 270,589

[22] Filed: Jul. 5, 1994

[30] Foreign Application Priority Data

Jul. 7, 1993 [JP] Japan .................................. 5-192753

[51] Int. Cl.$^6$ .................................................. A01N 43/56
[52] U.S. Cl. ........................................... 514/404; 514/912
[58] Field of Search ........................ 548/371.1; 514/403, 514/912, 404

[56] References Cited

U.S. PATENT DOCUMENTS

| | | | |
|---|---|---|---|
| 3,468,665 | 9/1969 | Misu et al. | 548/371.1 |
| 4,857,542 | 8/1989 | Nishi et al. | 514/404 |

FOREIGN PATENT DOCUMENTS

| | | |
|---|---|---|
| 0 125 406 | 11/1984 | European Pat. Off. . |
| 0 208 874 | 1/1987 | European Pat. Off. . |
| 3 533 662 | 3/1986 | Germany . |
| WO93/00088 | 1/1993 | WIPO . |

OTHER PUBLICATIONS

Zigler et al., "Cataracts in the Royal College of Surgeons Rat; Evidence for Initiation by Lipid Peroxidation Products", Exp. Eye Res. (1985) 41, 67–76.
Bhuyan et al., Current Eye Research, vol. 3, No. 1 (1984) pp. 67–81.
Babizhayev, Acta Ophthalmologica, vol. 67, No. 3 (1989) pp. 281–287.
Armstrong et al., Free Radical Biology & Medicine, vol. 11, No. 4 (1991) pp. 433–436.
Mitsubishi Kasei, Database WPOI, Week 9144, Derwent Publications Ltd., London AN 91–321587 JP–A–3215426, 1991.
Zondlo et al., Journal of The American College of Toxicology, vol. 11, No. 4 (1992) pp. 475–488.

*Primary Examiner*—Shean C. Wu
*Attorney, Agent, or Firm*—Wenderoth, Lind & Ponack, L.L.P.

[57] ABSTRACT

A pharmaceutical composition useful for prophylactic or therapeutic treatment of ophthalmological diseases, comprising 3-methyl-1-phenyl-2-pyrazolin-5-one or a pharmaceutically acceptable salt thereof as an essential component. The pharmaceutical composition of the present invention is useful for treating various types of ophthalmological diseases, particularly cataract and retinal diseases caused by aging and diabetes mellitus, and also both congenital and inherent cataracts due to drugs, external wound, etc.

3 Claims, 3 Drawing Sheets

PHARMACEUTICAL COMPOSITION USEFUL FOR TREATING OPHTHALMOLOGICAL DISEASES

The present invention relates to a pharmaceutical composition useful for prophylactic or therapeutic treatment of ophthalmological diseases and, more particularly, it relates to a pharmaceutical composition which comprises 3-methyl-1-phenyl-2-pyrazolin-5-one or a pharmaceutically acceptable salt thereof as an essential component.

An increase in lipid peroxides in the eyeball due to aging or diabetes mellitus is believed to be a direct cause for ophthalmological diseases, particularly for cataract and retinal diseases (Free Radical no Rinsho, 2, 179–183(1987); Saishin Igaku, 33, 726–729(1978)). It has been also presumed that an increase in the lipid peroxide content in the eyeball may participate in the occurrence of both congenital cataract and acquired cataract due to drugs or trauma and, moreover, retinopathy of prematurity (Free Radical no Rinsho, 2, 179–183(1987); Ganka Kiyo, 29, 119–127(1978) ). Thus, in such diseases, it has been known that concentrations of glutathione, ascorbic acid, etc., which are biological radical scavengers (in vivo), are lowered, whereby peroxidation of lipids proceeds in the tissues, which causes an increase in the concentration of lipid peroxide.

Additionally, lipid peroxide in blood easily moves into the eyeball and, as a result thereof, the concentration of lipid peroxide in the eyeball further increases. The lipid peroxides accumulated in the eyeball injure the crystalline lens and the retina by oxidation, which is one of the major factors causing the cataract and the retinal diseases.

Therefore, it is expected that supplementation of exogenous radical scavenger to the eyeballs with deficiency in biological radical scavenger for the purpose of inhibiting lipid peroxidation may prevent the occurrence or the progress of the ophthalmological diseases such as cataract and retinal diseases. In clinics, the above-mentioned glutathione has been used as a remedy for cataract. However, some problems such as the fact that glutathione exhibits poor permeability through membranes have been reported, and there has been a demand for new drugs.

The present inventors formerly found, using actual pathological models that certain types of pyrazolone derivatives exhibited a potent inhibitory action against lipid peroxidation and showed a protective action to cerebral ischemic diseases and myocardial ischemic disorders mainly caused by the peroxidation of lipids due to active oxygens (Japanese Patent Publication [Examined] Hei-5/35127). Paying attention to such pyrazolone derivatives, the present inventors have investigated their usefulness as a therapeutic agent for treating ophthalmological diseases and found that 3-methyl-1-phenyl-2-pyrazolin-5-one (hereinafter, this compound will be sometimes referred to as "MCI-186") or a pharmaceutically acceptable salt thereof (hereinafter, both of these compounds will be sometimes collectively referred to as "the present compound") was able to prevent the occurrence or the progress of the ophthalmological diseases such as cataract and retinal diseases. The present invention is based on these findings.

Thus, one aspect of the present invention is directed to a pharmaceutical composition useful for prophylactic or therapeutic treatment of the ophthalmological diseases, comprising as an essential component 3-methyl-1-phenyl-2-pyrazolin-5-one or a pharmaceutically acceptable salt thereof. Another aspect of the present invention is directed to a method of prophylactically or therapeutically treating ophthalmological diseases by the use of the present compound. A further aspect of the invention is directed to the use of the present compound for preparing a pharmaceutical composition for treating ophthalmological diseases.

The present compound which is an essential component of the pharmaceutical composition according to the present invention is described in the above-mentioned Japanese Patent Publications [Examined] Hei-5/35128 and Hei-5/31523 and can be manufactured by a method disclosed in those publications or by methods similar thereto.

Examples of the pharmaceutically acceptable salt of MCI-186 are the salts with a mineral acid such as hydrochloric acid, sulfuric acid, hydrobromic acid, phosphoric acid, etc.; the salts with an organic acid such as methanesulfonic acid, p-toluenesulfonic acid, benzenesulfonic acid, acetic acid, glycolic acid, glucuronic acid, maleic acid, fumaric acid, oxalic acid, ascorbic acid, citric acid, salicylic acid, nicotinic acid, tartaric acid, etc.; the salts with an alkali metal such as sodium, potassium, etc.; the salts with an alkali earth metal such as magnesium, calcium, etc.; and the salts with ammonia or with an amine such as tris (hydroxymethyl)aminomethane, N,N-bis(hydroxyethyl) piperazine, 2-amino-2-methyl-1-propanol, ethanolamine, N-methylglucamine, L-glucamine, etc.

In the clinical application of the present compound, the present compound is used either as it is or as a pharmaceutical composition formulated with a pharmaceutically acceptable vehicle. When used as an eye lotion, it is preferred that one to two drops of 1–20 mg/ml of the present compound are applied to the eye one to several times a day; when used orally, it is preferred that 1–100 mg/kg of the present compound is administered one to three times a day; and, in the case of an intravenous injection, it is preferred that 0.01–10 mg of the present compound is administered two to five times a day. It is also preferable that said dose is subjected to a continuous drip infusion. In the case of a rectal administration, it is preferred that 1–100 mg/kg of the present compound is administered one to three times a day. The above-mentioned dose may be changed depending upon the age, the state of the disease, the sex, the symptom, etc., of particular patients.

The form of the pharmaceutical composition, i.e. the pharmaceutical formulation, includes an aqueous eye drop, a nonaqueous eye drop, a suspended eye drop, an emulsified eye drop, etc., in the case of the ophthalmolgic formulations. Manufacture of the eye drops is carried out by dissolving or suspending the present compound in an aqueous solvent such as sterilized distilled water, physiological saline solution, etc., or in a nonaqueous solvent such as plants oil including cottonseed oil, soybean oil, sesame oil, peanut oil, etc. If necessary, suitable amounts of isotonizing agents, pH adjusting agents, thickeners, suspending agents, emulsifiers, preservatives, etc., may be added thereto. Examples of the isotonizing agent are sodium chloride, boric acid, sodium nitrate, potassium nitrate, D-mannitol, glucose, etc.; examples of the pH adjusting agents are boric acid, anhydrous sodium sulfite, hydrochloric acid, citric acid, sodium citrate, acetic acid, potassium acetate, sodium carbonate, borax, etc.; examples of the thickener are methyl cellulose, hydroxypropylmethyl cellulose, polyvinyl alcohol, sodium chondroitinsulfate, polyvinylpyrrolidone, etc.; examples of the suspending agent are polysorbate 80, polyoxyethylene hydrogenated castor oil 60, polyoxy castor oil, etc.; examples of the emulsifier are egg yolk lecithin, polysorbate 80, etc.; and examples of the preservative are benzalkonium chloride, benzethonium chloride, chlorobutanol, phenylethyl alcohol, p-hydroxybenzoates, etc.

In pharmaceutical formulations other than eye drops, the present compound may be used together with conventionally-used pharmaceutical vehicles such as a bulking agent or other additives. Such vehicles may be either solid or liquid. Examples of the solid vehicle are lactose, kaolin, sucrose, crystalline cellulose, corn starch, talc, agar, pectin, acacia, stearic acid, magnesium stearate, lecithin, sodium chloride, etc., while examples of the liquid vehicle are syrup, glycerol, peanut oil, polyvinylpyrrolidone, olive oil, ethanol, benzyl alcohol, propylene glycol, water, etc.

When a solid vehicle is used, the formulations may be in the form of tablets, diluted powder, granules, hard gelatin capsules, suppositories, troches, etc. In these formulations, the amount of the solid vehicle is not critical. Preferably, however, it is from about 1 mg to about 1 g.

When a liquid vehicle is used, the formulation may be in the form of syrups, lotions, soft gelatin capsules, sterilized solutions for injection or aqueous or nonaqueous suspensions.

It is also preferred that, in the manufacture of the pharmaceutical formulations according to the present invention, the present compound is formulated into a sustained-released form by, for example, modifying the compound into an inclusion compound using cyclodextrin or placing it in liposomes.

The pharmaceutical composition of the present invention prepared as such is used as a drug for the prophylactic or therapeutic treatment of various types of ophthalmological diseases such as cataract, retinal diseases, etc.

BRIEF EXPLANTION OF THE DRAWING

The present invention will be further illustrated by way of the following examples although the present invention is not limited thereto.

EXAMPLE 1

An Action of Preventing the Nebula of the Extracted Eyeball

1) Manufacture of Formulations m-Chloroperoxybenzene (hereinafter abbreviated as "MCPBA") (30 mg) was dissolved in 0.5 ml of ethanol of a special grade, 50 ml of distilled water was added thereto, the mixture was adjusted to pH 7.0 with 1N NaOH, and the total volume was made 100 ml using distilled water. Hereinafter, the resultant solution will be referred to as "MCPBA solution".

Distilled water was added to 0.5 ml of ethanol of a special grade to make the total volume 100 ml. Hereinafter, the resultant solution will be referred to as "Vehicle-1".

MCI-186 was dissolved in 30 ml of 1N NaOH, the resultant solution was adjusted to pH around 8.0 by 1N HCl, and the total volume was made 100 ml using distilled water. Hereinafter, this mixture will be referred to as "test drug".

To 30 ml of 1N NaOH was added 1N HCl in order to adjust the pH to around 8.0, and the total volume was made 100 ml using distilled water. Hereinafter, this mixture will be referred to as "Vehicle-2".

2) Extraction of the Eyeball

Male gerbils (body weight: 80–100 g) were anesthetized by an intraperitoneal administration of 45 g/kg of pentobarbital. Both eyes were carefully extracted so that they were not injured and then kept in an ice-cooled physiological saline until the study.

3) An Inhibitory Action against Nebula of the Eyeball

First, 0.4 ml of the Vehicle-2 was added to each 4 ml of the MCPBA solution or the Vehicle-1 and, if necessary, the pH was adjusted to around 7.5 using a small amount of 1N NaOH. One set of the eyeballs (one set comprised the extracted two eyeballs) was added thereto and kept in a dark place at 4° C. After 48 hours, the extracted eyeballs were investigated. The result was that, though no nebula on the eyeballs was observed in the combination of the Vehicle-1 and the Vehicle-2, the nebula was detected in the combination of the MCPBA solution and the Vehicle-2. Consequently, it is ascertained that the MCPBA solution causes the nebula on the eyeball.

Figure 1:
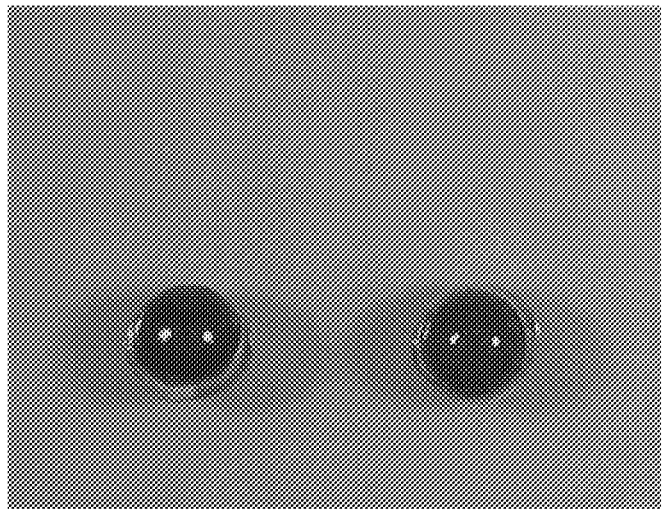
FIG. 1 is a photograph showing the result of the inhibitory test against nebula on the eyeballs of the gerbil using the Vehicle-1 and the Vehicle-2, as described in the working Example 1.
Figure 2:
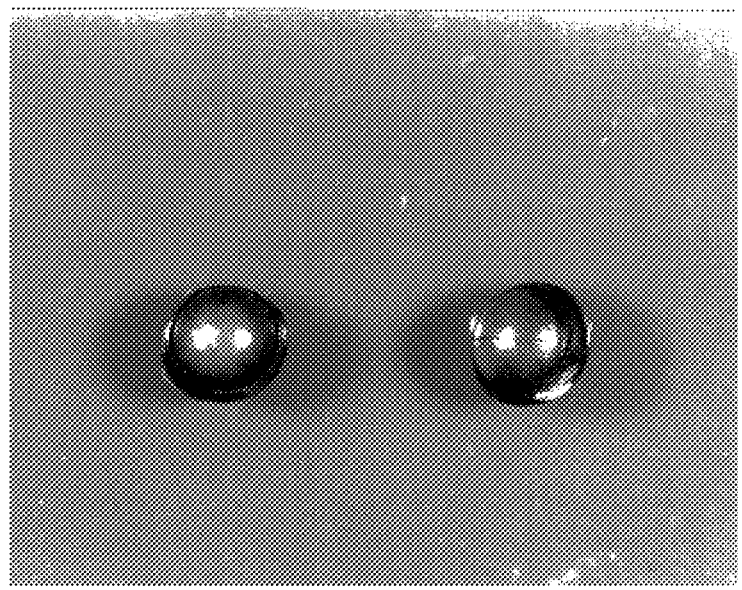
FIG. 2 is a photograph showing the result of the inhibitory test against nebula on the eyeballs of the gerbil using the MCPBA solution and the Vehicle-2, as described in the working Example 1.
Figure 3:
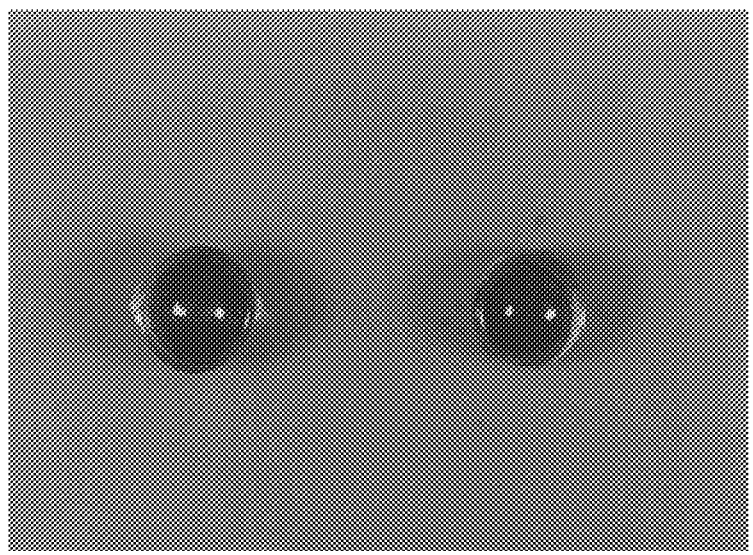
FIG. 3 is a photograph showing the result of the inhibitory test against nebula on the eyeballs of the gerbil using the MCPBA solution and the test drug, as described in the working Example 1.

Then, 0.4 ml of the test drug was added to 4 ml of the MCPBA solution and, if necessary, its pH was adjusted to around 7.5 by the addition of a small amount of 1N NaOH. A set of the extracted eyeballs was added thereto in the same manner as above and preserved in a dark place at 4° C. After 48 hours, the extracted eyeballs were observed by naked eye. The result was that no nebula was found in the eyeballs like in the case of the above-mentioned combination of the Vehicle-1 and the Vehicle-2. Consequently, it was confirmed that the nebula on the eyeballs caused by the MCPBA was inhibited by the test drug, as shown in FIGS. 1–3 of the accompanying drawings.

EXAMPLE 2

An Inhibitory Action against the Cataract of the Growing Chicken Embryo

1) Manufacture of Formulations

Sodium hydrocortisone succinate (hereinafter, abbreviated as an "HC") was dissolved in distilled water.

MCI-186 was dissolved in 30 ml of 1N NaOH, the pH was adjusted to around 7.5 by the addition of 1N HCl, and the total volume was made 100 ml with distilled water. Hereinafter, the resultant solution will be referred to as "test drug".

2) An Inhibitory Action against Nebula of the Eyeballs

The cataract model was prepared according to the method of Nishigori, et al (Experimental Eye Research, 36, 617–622 (1983)). Thus, 0.30 micromoles/egg of HC was administered to the air chamber of an egg. After 4, 8 and 24 hours, 1.5 or 5.0 micromoles/egg of the test drug or 0.1 ml of a physiological saline solution (control) was administered to the air chamber. After 48 hours from the administration of the HC, the eyeballs were extracted and the degree of nebula was observed by the method of Nishigori, et al.

The test results are shown below.

TABLE 1

| Group (Number of eyeballs tested) | Number of eyeballs for Each Score | | | | | | Average Score | Rate (%) to the Control |
|---|---|---|---|---|---|---|---|---|
| | 0 | 1 | 2 | 3 | 4 | 5 | | |
| Control (18) | 0 | 1 | 0 | 5 | 2 | 10 | 4.1 | 100 |
| Test Drug a (18) | 2 | 0 | 2 | 5 | 4 | 5 | 2.9 | 70.0 |
| Test Drug b (18) | 4 | 3 | 8 | 0 | 1 | 2 | 1.9 | 47.1 |

Test Drug a: 1.5 micromoles/egg (three times)
Test Drug b: 5.0 micromoles/egg (three times)
0: Transparent crystalline lens
1: Partial nebula around the nucleus of the crystalline lens
2: Slight ring-like nebula around the nucleus of the crystalline lens
3: Clear ring-like nebula round the nucleus of the crystalline lens
4: The ring-like nebula around the crystalline lens spread to the center
5: Crystalline lens was completely in the state of nebula both in the center and around the nucleus.

The above test result confirmed that the test drug containing MCI-186 as an essential component inhibited the nebula in the eyeball of the growing chicken embryo caused by HC.

The pharmaceutical composition of the present invention is useful for prophylactically and therapeutically treating various types of ophthalmological diseases, particularly cataract or retinal diseases caused by aging and diabetes mellitus, and also both congenital and acquired cataracts due to drugs, external wound, etc.

We claim:

1. A method of prophylactic or therapeutic treatment of an ophthalmological disease caused by an increase in lipid peroxide in the eyeball in mammals, characterized by administering an effective amount of 3-methyl-1-phenyl-2-pyrazolin-5-one or a pharmaceutically acceptable salt thereof to said mammals susceptible to or suffering from said diseases.

2. The method according to claim 1, wherein the ophthalmological disease is cataract.

3. The method according to claim 1, wherein the ophthalmological disease is retinal disease.

* * * * *